(12) United States Patent
Orth et al.

(10) Patent No.: US 9,949,807 B2
(45) Date of Patent: Apr. 24, 2018

(54) DRILL GUIDE FOR A DENTAL IMPLANT AND A METHOD FOR FABRICATING A DRILL GUIDE

(75) Inventors: Ulrich Orth, Heppenheim (DE); Sascha Schneider, Mühltal (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 13/983,524

(22) PCT Filed: Feb. 2, 2012

(86) PCT No.: PCT/EP2012/051724
§ 371 (c)(1),
(2), (4) Date: Aug. 2, 2013

(87) PCT Pub. No.: WO2012/104361
PCT Pub. Date: Aug. 9, 2012

(65) Prior Publication Data
US 2013/0309628 A1 Nov. 21, 2013

(30) Foreign Application Priority Data

Feb. 3, 2011 (DE) .................. 10 2011 003 557

(51) Int. Cl.
*A61C 3/00* (2006.01)
*A61C 8/00* (2006.01)
*A61C 1/08* (2006.01)

(52) U.S. Cl.
CPC ............ *A61C 8/0089* (2013.01); *A61C 1/084* (2013.01); *Y10T 29/49567* (2015.01)

(58) Field of Classification Search
CPC ........ A61C 1/084; A61C 8/0089; A61C 1/082
(Continued)

(56) References Cited

U.S. PATENT DOCUMENTS

| 4,840,564 A | 6/1989 | Segal |
| 5,297,060 A | 3/1994 | Foletti et al. ................ 364/559 |

(Continued)

FOREIGN PATENT DOCUMENTS

| DE | 199 52 962 A1 | 5/2001 |
| DE | 10 2005 040 738 A1 | 3/2007 |

(Continued)

OTHER PUBLICATIONS

International Search Report from International Application No. PCT/EP2012/051724, dated Jan. 22, 2013.

(Continued)

*Primary Examiner* — Cris L Rodriguez
*Assistant Examiner* — Matthew Saunders
(74) *Attorney, Agent, or Firm* — Fitzpatrick, Cella, Harper & Scinto

(57) ABSTRACT

A drill guide for creating a drilled implant hole for a dental implant, and a method for producing the drill guide. The drill guide includes a base part having at least one access opening and at least one sleeve. A first surface of the base part has an impression of a preparation site, and a second surface of the base part opposite the first surface has a support surface. The access opening expands from the second surface to the first surface of the base part. The access opening and the support surface are shaped in such a way that the sleeve can be inserted at least partially into the access opening, and the sleeve, when inserted, rests on the support surface and is positioned and oriented relative to the base part.

15 Claims, 4 Drawing Sheets

(58) Field of Classification Search
USPC .................................................. 433/72–75
See application file for complete search history.

(56) References Cited

U.S. PATENT DOCUMENTS

| | | | | |
|---|---|---|---|---|
| 5,641,287 | A * | 6/1997 | Gittleman | A61B 17/176 433/75 |
| 5,967,777 | A * | 10/1999 | Klein et al. | 433/75 |
| 6,319,006 | B1 | 11/2001 | Scherer et al. | 433/214 |
| 2004/0078212 | A1 * | 4/2004 | Andersson | G06Q 10/103 433/215 |
| 2004/0219479 | A1 | 11/2004 | Malin et al. | 433/75 |
| 2006/0105291 | A1 | 5/2006 | Stein et al. | |
| 2007/0059665 | A1 | 3/2007 | Orentlicher et al. | 433/173 |
| 2007/0154862 | A1 | 7/2007 | Kim | |
| 2007/0281270 | A1 | 12/2007 | Brajnovic | |
| 2008/0064005 | A1 | 3/2008 | Meitner | 433/74 |
| 2008/0287953 | A1 | 11/2008 | Sers | 606/87 |
| 2009/0136902 | A1 * | 5/2009 | Zundorf | A61C 8/0089 433/223 |
| 2011/0111362 | A1 * | 5/2011 | Haber | 433/72 |
| 2013/0224685 | A1 | 8/2013 | Cheng et al. | |

FOREIGN PATENT DOCUMENTS

| | | | |
|---|---|---|---|
| DE | 10 2005 040 739 A1 | 3/2007 | |
| DE | 10 2008 008 763 A1 | 8/2009 | |
| DE | 10 2009 008 790 B3 | 5/2010 | |
| DE | 10 2010 012 960 A1 | 9/2011 | |
| EP | 0 269 354 A1 | 6/1988 | |
| EP | 1 502 556 A2 | 2/2005 | |
| GB | 2 061 512 A | 5/1981 | |
| GB | 2 246 729 A | 2/1992 | |
| JP | 63-212348 S | 9/1988 | |
| JP | 2001-523509 A | 11/2001 | |
| JP | 2007-512079 A | 5/2007 | |
| JP | 2008-508931 A | 3/2008 | |
| JP | 2012-110723 A | 6/2012 | |
| WO | WO 1999/32045 A1 | 7/1999 | |
| WO | WO 2004/076106 A1 | 9/2004 | |
| WO | WO 2005/053567 A1 | 6/2005 | |
| WO | WO 2005053566 A1 * | 6/2005 | A61C 1/084 |
| WO | WO 2005/120385 A1 | 12/2005 | |
| WO | WO 2009/118391 A1 | 10/2009 | |

OTHER PUBLICATIONS

English language translation of International Search Report from International Application No. PCT/EP2012/051724, dated Jan. 22, 2013.

Straumann, "Herstellung Und Anwendung Einer Individuellen Borschablone," Dec. 2007, 6 sheets (with machine translation, 4 sheets).

International Search Report and Written Opinion (German-language), issued in connection with International Application No. PCT/EP2012/051724, dated Jan. 30, 2013, 15 sheets (with translation, 15 sheets).

International Preliminary Report on Patentability (German-language), issued in connection with International Application No. PCT/EP2012/051724, dated Aug. 6, 2013, 10 sheets (with translation, 13 sheets).

German Office Action issued in connection with German Application No. 10 2011 003 557.5, dated Jul. 14, 2011, 5 sheets (with machine translation, 5 sheets).

Extended European Search Report issued in connection with European Application No. 13179734.2, dated Jan. 7, 2014.

Office Action, Japanese Patent Appln. No. 2013-552196 dated Dec. 22, 2015, Japanese Patent Office.

* cited by examiner

DRILL GUIDE FOR A DENTAL IMPLANT AND A METHOD FOR FABRICATING A DRILL GUIDE

The present application is a national-stage entry under 35 U.S.C. § 371 of International Application No. PCT/EP2012/051724 filed on Feb. 2, 2012, and claims the benefit of foreign priority under 35 U.S.C. § 119 of German Application No. 10 2011 003 557.5 filed on Feb. 3, 2011. Each of these applications is incorporated herein in its entirety, as if set forth fully herein.

TECHNICAL FIELD

The invention concerns a drill guide for making a drilled implant hole for a dental implant including a base part with at least one access opening and at least one sleeve, wherein a first surface of the base part features a dental impression of a preparation site, wherein a second surface of the base part located opposite features a support surface.

PRIOR ART

A number of drill guides with access openings and sleeve inserts, for the creation of proposed drilled implant holes with a certain orientation and a certain position, into which dental implants can then be inserted, are known from the prior art.

A drill guide with a guide sleeve for guiding an oral surgery drill is disclosed in DE 10 2009 008 790 B3. The drill can also be inserted into the guide sleeve where there is minimal space, if this has a slot in its peripheral surface running at an angle relative to the longitudinal axis of the sleeve. In addition, this type of guide sleeve allows an almost optimal guidance for the drill in the direction of the proposed drilling axis.

The guide sleeve can be braced via fixtures in the drill guide. The fixture can be designed as a part of a change mechanism, by means of which the sleeve can be detachably attached to a bracket. The change mechanism can include a tapered element and an associated bracket, which can be connected so as to interlock.

The handbook, "Fabrication and Application of a Customized Drill Guide", from Straumann GmbH, discloses a fabrication method for a drill guide. In a first step, a plaster situational model is produced. In a second step, a plastic splint is thermoformed on the situational model. In a third step, a second plaster cast is produced, sawn into sections taking the proposed implant position into account, the measured bony profile is transferred and an implant axis is determined. In the fourth step, a wax-up of the proposed restoration is fabricated on the original situational model. In a fifth step, a duplicate of the wax-up model is fabricated and a plastic splint is thermoformed on this. In a sixth step, the new plastic splint is transferred to the situational model. In a seventh step, the implant position and implant axis determined are marked on the situational model and the drilling is performed using a parallelometer and a pilot drill. In an eighth step, a titanium pin is inserted into the drilled hole. In a ninth step, a new plastic splint is thermoformed over the titanium pin inserted in the model. In a tenth step, the plastic splint is removed from the model and the titanium pin is replaced by a shorter titanium pin. In an eleventh step, the plastic splint is placed on the previously fabricated model marked with the bony profile and the implant axis is verified. If required, the position and direction of the drilled hole can still be corrected. In a twelfth step, a titanium pin with a gradation is inserted into the drilled hole and any potential undercuts are blocked with plaster, wax or plastic. A new plastic splint is thermoformed over the titanium pin with gradation. After removing the titanium pin with gradation, an occlusal opening is cut or ground in the plastic splint and a drilling sleeve with an edge is inserted into the plastic splint. The plastic splint is then ground or cut in the region of the implant site. Alternately, in the ninth step, a drilling sleeve can be placed over the titanium pin and this drilling sleeve can be fixed with plastic or plaster. A plastic splint is then thermoformed over the drilling sleeve and the drilled hole is reamed out to admit the pilot drill.

DE 199 52 962 AI discloses a method for creating a drill guide for a dental implant, wherein an X-ray image of the jaw is taken initially and a three-dimensional visual measurement of the visible surface of the jaw and the teeth is then made. The measurement datasets from the X-ray image and the three-dimensional visual recording are correlated with one another. By reference to the information available, such as the type and the location of the implant relative to the adjacent teeth, a template is designed and created, which is supported on the adjacent teeth and thus, precise drilling of the implant feed hole is enabled. By reference to the X-ray data, the implant can be specified and positioned in the established fashion. By reference to the data obtained about the surface structure, i.e. the occlusal surfaces of adjacent teeth, an implant aid in the form of a drill guide can be milled by means of a CAD/CAM unit. By reference to the measurement data, a CAD/CAM device is able to fabricate the drilling template and a drill guide for the drill using the negative of the occlusal surfaces. An end stop is positioned on the drilling template, which determines the drilling depth.

WO 99/32045 discloses a method for fabricating a dental drill guide for implants. First, a three-dimensional computer image is modeled using an image of the jaw with reference to an impression surface. The position and the drilling depth of the drilled holes are then determined and a set of drilled implant hole coordinates is entered into a computer-controlled fabrication machine. Using a precision tool, a drill guide socket is prepared beforehand in the drilling template for each of the sets of coordinates for the drilled holes entered in a position corresponding to the position and orientation of the drilled holes determined by reference to the section of the jaw.

One disadvantage of this method is in that the majority of CAD/CAM machines have restricted degrees of freedom and particularly that drilled holes arranged out of square with each other cannot be realized. For this reason, the fabrication of drill guides by means of a CAD/CAM machine is only possible for limited indication ranges. In most cases, the drill guide is either fabricated individually in the laboratory or centrally, after prior CAD/CAM planning, using a hexapod, for example, the design of which allows a flexibility of the object to be processed in all six degrees of freedom, and vertical drilled holes are placed by means of a parallelometer. Generally, CT-DVT templates, bite plates and plaster models of the jaw are used in the central fabrication. These are assembled on the lavishly designed hexapod and are adjusted with the aid of multiple measuring points. This process is very elaborate and hence also prone to error.

The object of this invention is to make a method available that enables the fabrication of any drill guide, particularly with out of square drilling axes, using a conventional fabrication machine with limited degrees of freedom.

DESCRIPTION OF THE INVENTION

The invention concerns a drill guide for the creation of a drilled implant hole for a dental implant comprising a base part with at least one access opening and at least one sleeve. A first surface of the base part has a dental impression of a preparation site, wherein a second surface of the base part, located opposite, has a support surface. Starting from the second surface, the access opening is flared toward the first surface of the base part, wherein the access opening and the support surface of the base part are molded so that the sleeve can be at least partially inserted into the access opening and the sleeve, when inserted, rests on the support surface and is positioned and oriented relative to the base part.

The dental drill guide can be any drill guide, such as a drill guide supported by the adjacent teeth for minimal invasive surgery or a drill guide supported by the jawbone for so-called open-flap surgery.

The drill guide is used to guide a drill, in order to create the proposed drilled implant hole to position an implant as calculated in the implant planning. The sleeve is inserted into the access opening on the first surface of the access opening, wherein the inner surface of the sleeve serves to guide the drill. An X-ray image of the jaw and a three-dimensional visual measurement of the visible surface of the jaw and the teeth can be used in the implant planning in order to determine an implant type and the implant positions relative to the jaw virtually. In particular, the precise position, the angle relative to the jaw and the depth of the drilled implant holes for inserting the implants are planned. The drill guide is provided for the creation of one or more drilled implant holes, which can also be arranged out of square with each other. The cast of the point of oscillation on the first surface of the base part corresponds to a negative analog to the surface of the preparation site or to a cast of the teeth adjacent to the preparation site. The flared access opening between the first surface and the second surface of the base part can be designed in any shape. In particular, the access opening can be formed so as to taper, with an oval or circular base. At the same time, the sleeve can have a cylindrical sleeve part that fits into the access opening. The sleeve can have a disk-shaped sleeve part that, when inserted, rests on the support surface of the base part and thus, the position and orientation of the sleeve relative to the base part is determined. At the same time, the diameter of the access opening can be greater than the diameter of the cylindrical sleeve part, so that the position of the sleeve is defined by the support surface alone.

One advantage of the drill guide is that the access opening is flared and can thus be milled by means of a conventional machine tool with three or four axes. Hence, the drill guide can be fabricated quickly and easily, directly in the dental office, using any conventional machine tool with limited degrees of freedom. Hence, fabricating the drill guide using more complex machine tools based on planning data in a central laboratory is no longer necessary.

A further advantage of the drill guide is that the orientation and position of the sleeve relative to the base part can be corrected if it is determined on inspection that the measured position and orientation values do not correspond to the target values specified by the implant planning. At the same time, the support surface can be corrected using the machine tool. With conventional drill guides with cylinder-shaped drilled access holes, this type of correction of the orientation and the position of the drilled guide holes is no longer possible.

The sleeve can be manufactured from metal and the base part from a plastic, which is as easy as possible to process, and can be transparent.

Advantageously, the base part can have an end stop on the second surface, which is designed so that the sleeve rests on the support surface when inserted and is laterally in contact with the end stop.

Thus, when inserted, the sleeve is delimited laterally by the end stop and hence is fixed in position. The end stop can be designed, for example, in the form of a gradation with an angle of 90°, which is designed as an analog to the disk-shaped sleeve part. The end stop can also be shaped in the form of straight surfaces, which have end positions on the sleeve when inserted. The end stop can be milled using a machine tool with limited degrees of freedom with three or four axes.

Advantageously, one lateral surface of the flared access opening can form an opening angle of at least 15° to an axis of the sleeve when inserted.

The flared access opening can thus be milled by means of the machine tool with limited degrees of freedom with three or four axes. Milling cylindrical drilled holes with any orientation is not possible using this type of machine tool.

Advantageously, the flared access opening can be tapered and can have a first radius on the first surface and a second radius on the second surface. The sleeve can have a disk-shaped first sleeve part and a cylinder-shaped second sleeve part with a locating channel, wherein the second radius of the access opening on the second surface of the base part can be adapted to the cylinder-shaped second sleeve part. The second radius of the access opening can be at least as large as one radius of the second sleeve part.

The tapered, flared access opening is thus milled to match the cylinder-shaped second sleeve part. At the same time, the sleeve is positioned by placing the first disk-shaped sleeve part on the support surface. The second radius of the access opening should preferably correspond to the radius of the cylinder-shaped second sleeve part. Hence, the sleeve, when inserted, is fixed in a lateral direction.

Advantageously, the sleeve can have a third sleeve part with a locating channel, which, starting from the support surface, is aligned in a direction away from the base part.

The second sleeve part, which is inserted into the access opening, can thus be realized with smaller dimensions, wherein the locating channel in the third sleeve part is measured to such a length as to guarantee precise guiding of the drill for creating the drilled implant hole.

Advantageously, the sleeve can be prefabricated. The base part can be fabricated using a limited machine tool with three or four machining axes.

The sleeve can be prefabricated, for example, using a CAM machine tool with five or more machining axes. The sleeve can also be prefabricated using a sintering technique, another production method. Multiple sleeves with various locating channels for different drills can also be prefabricated and made available in an assortment for creating the drill guide.

Because of the flared access opening, the base part itself can also be fabricated using a CAM machine tool with limited degrees of freedom.

A further object of the invention is a method for fabricating a dental drill guide, which has a base part with at least one access opening and at least one sleeve. As well, a cast of a preparation site is already in place on a first surface of the base part. In a first step, a support surface, shaped to match a supporting part on the sleeve, is elaborated on a second, opposing surface of the base part. In a second step, an access opening is formed, which is flared starting from the second surface toward the first surface of the base part. At the same time, the access opening and the support surface of the base part are shaped such that the sleeve can be at least partially inserted into the access opening and the sleeve, when inserted, rests above the supporting part on the support surface and is positioned and oriented relative to the base part.

The support surface of the base part can be formed, for example, in a ring-shaped arrangement as an analog to the disk-shaped supporting part of the sleeve. The machining can be performed in a machine tool with limited degrees of freedom with three or four axes. The access opening can also be formed, for example, in the limited machine tool. The flared access opening is shaped so that a cylinder-shaped sleeve part can be inserted into the sleeve at least on the second surface of the base part. The sleeve incorporates a locating channel, which serves to guide the drill.

One advantage of the method according to the invention is that the drill guide can be machined using a conventional machine tool with three or four axes, which is available in many dental offices. Hence, transferring the planning data and central fabrication in a dental laboratory is no longer necessary.

A further advantage of the method according to the invention is that a subsequent correction of the support surface in order to correct the position and the location of the sleeve relative to the base part can be made in the machine tool. After the creation of the drilled guide holes, this type of correction of the drilled guide holes can no longer be performed on conventional drill guides. Correcting the support surface is necessary if it is determined on inspection that the measured position and orientation values do not correspond to the target values specified by the implant planning. In conventional drill guides with cylinder-shaped drilled access holes, this type of correction of the orientation and the position of the drilled guide holes is no longer possible.

Advantageously, the sleeve on the second surface of the base part can be inserted into the axis opening in a further step, until the supporting part comes into contact with the support surface of the base part, wherein the sleeve can then be fixed onto the base part by means of an adhesive process.

The sleeve is thus inserted into the access opening until the disk-shaped supporting part of the sleeve comes into contact with, for example, a ring-shaped support surface of the base part. The sleeves are then firmly bonded to the base part by adhesion. The drill guide according to the invention is thus completed. The position and orientation of the sleeves relative to the base part can be examined prior to the process of bonding the sleeves to the based part and, if necessary, the support surface can be corrected.

The drill guide according to the invention can have multiple access openings with multiple sleeves, set at an oblique angle to one another.

Advantageously, an end stop can be formed on the base part on the second surface, which is designed so that, when inserted, the supporting part of the sleeve is delimited laterally in respect of an axis of the sleeve by the end stop.

The end stop can thus be ground or milled, for example, by means of the limited machine tool. The end stop can be shaped, for example, as a gradation, which is designed as an analog to a disk-shaped sleeve part, for example. The axis of the sleeve can be the axis of symmetry corresponding to an axis of the locating channel of the sleeve.

Advantageously, a CAM technique using a grinding tool and/or a milling tool can be used to elaborate the support surface and the access opening.

A conventional CAM machine tool with a grinding tool or a milling tool can thus be used to perform the method according to the invention. This type of machine tool is already available in many dental offices, and so the drill guide can be manufactured directly in the dental office.

Advantageously, a machine tool with three or four machining axes can be used.

The drill guide according to the invention can thus be fabricated by means of a limited machine tool with only three or four machining axes.

Advantageously, the sleeve can be prefabricated using a machine tool with at least five machining axes.

The sleeve can also be prefabricated using another production method, such as by sintering. An assortment with multiple sleeves for different drills can also be prefabricated for performing this method.

Advantageously, certain areas of the cast can be shaped, whereas other areas of the cast can remain untreated and can serve as contact areas of the base part.

In this process step, the cast of the preparation in particular is flared to the extent that certain contact areas remain, so that this ensures that the drill guide can be positioned on the preparation with a precise fit and comes into contact with the remaining dentition in the contact areas provided.

The proposed depth of the drilled implant hole can also be taken into consideration in the planning for the support surface of the base part, wherein the inserted sleeve serves as a depth stop. Alternately, a separate depth stop can be milled in the machine tool. This determines the penetration depth of the drill.

Advantageously, the flared access opening can be shaped so as to taper, wherein this can have a first radius on the first surface and a second radius on the second surface of the base part. At the same time, the sleeve can have a disk-shaped first sleeve part and a cylinder-shaped second sleeve part with a locating channel. The second radius of the access opening on the second surface of the base part can be adapted to the cylinder-shaped second sleeve part as well, wherein the second radius of the access opening can be formed to be at least as large as a radius of the second sleeve part.

The flared access opening can thus be milled so as to taper in the machine tool, wherein the second radius of the access opening on the second surface of the base part should preferably correspond to the radius of the cylinder-shaped second sleeve part, in order to secure the sleeve laterally when inserted. Hence, the position and orientation of the sleeve part, when inserted, can be controlled by means of the design of the flared access opening, of the end stop and of the contact surface.

A further object of the invention is a device for validating the fabricated drill guide. Here, the drill guide has at least one locating channel. The device has at least one pin and one disk, wherein the pin can be inserted into the locating channel. The disk is arranged at an adjustable distance above the drill guide and markings are provided on the disk for reading the position. The pin, the disk and the drill guide to be validated are shaped and arranged together so that the pin indicates a position on the disk, which can be read off by means of the markings.

In comparison with a known validation method, in which pins are inserted into drilled guide holes in a drill guide and a check is then made as to whether the lower ends of the pins correspond to markings on a printed checksheet, this method has the advantage that printing a checksheet is not necessary.

A further advantage is that this device enables a more precise validation of the position and the pitch of the locating channel since, in a validation using a checksheet, the drill guide is placed on the checksheet, and so the distances between the drilled guide holes and the checksheet are too small to detect deviations in the pitch and the position of the drilled guide holes reliably. With the present device, the dimensions of the pins can be designed to be sufficiently long for the distance between the drill guide and the disk to be large enough to guarantee a reliable measurement of the pitch and the position of the locating channels.

Advantageously, the disk can be a glass disk that can be arranged at a certain distance from the drill guide so that it comes into contact with an upper tip of the pin, wherein the location of the upper tip of the pin can be read off using the markings on the disk.

The fabricated drill guide can have one locating channel or multiple locating channels for multiple drilled implant holes. An insertable sleeve is positioned on the base part for each of the locating channels and is firmly bonded to this. The coordinates of the location of the pin on the disk can be read off and the precise pitch and position of the respective locating channel can be determined from this.

Advantageously, the disk can alternately be fabricated from a partially transparent material. The pin can have a laser oriented along an axis of the pin that projects a point of light onto the disk, and so when the pin is inserted into the locating channel, the laser on the pin points to a location on the disk, which can be read off by means of the markings on the disk.

In this alternate embodiment, the disk does not have to be brought into contact with the upper tip of the pin in order to read off the location. Any desired clearance can thus be set between the disk and the drill guide.

Advantageously, the markings on the disk can display crosshairs with an x axis and a y axis.

Concrete coordinates can thus be read on the crosshairs.

Advantageously, the device can have a support shaped so as to match a support face of the drill guide, wherein the relative location between the support face of the drill guide and the locating channel and between the support and the disk is known.

The drill guide can thus be precisely positioned relative to the device.

Advantageously, the device can have a magnifier arranged above the disk, which is used for reading off the markings on the disk.

The marking on the disk can thus be magnified in order to guarantee better legibility. The upper tip of the pin can be designed so as to taper in order to be able to determine clearly the location of the upper tip on the disk. The lower end of the pin can be designed as desired.

Advantageously, the pin can be designed as a cylinder, wherein, when the pin is inserted into the locating channel, a lower end of the pin comes into contact with a baseplate of the device.

In this embodiment of the pin, the pitch and the position of the locating channel can be calculated by reference to the length of the pin, the clearance between the baseplate and the disk and by reference to the coordinates of the upper tip of the pin, for example, using a design software program.

Advantageously, the pin can have a tapered supporting part in its central section that rests on the drill guide when inserted.

In this alternate embodiment, the lower end of the pin is not in contact with the baseplate of the device. When inserted, the pin rests on the inserted sleeve with the supporting part. Using design software, for example, the location and the pitch of the locating channel can be calculated by reference to the known clearance between the supporting part and the upper tip of the pin and by reference to the coordinates of the upper tip on the disk.

In this embodiment, the expected penetration depth of the drill can also be verified, wherein the dimensions of the lower part of the pin are designed so that the clearance between the lower tip of the pin and the supporting part corresponds to the penetration depth of the drill.

A further object of the invention is a method of validating a drill guide using the abovementioned device. The drill guide to be examined is positioned in a known location relative to the device, wherein the pin is inserted into the locating channel. The disk is arranged at a certain clearance to the drill guide, wherein a location on the disk, indicated by the pin, is read off using the markings.

In comparison to the known method using the checksheet, the present method has the advantage that a checksheet does not have to be printed out and the pitch and the position of the locating channel can be determined more precisely. The precise coordinates of the location on the disk are thus determined. The drill guide is thus position in a location relative to the validation device.

Advantageously, the disk can be arranged at a certain clearance to the drill guide so that it comes into contact with an upper tip of the pin, wherein the location of the upper tip of the pin is read off using the markings on the disk.

The location of the tip of the pin on the disk can thus be easily determined.

Advantageously, the orientation and the position of the locating channel can be verified using the coordinates of the location of the upper tip of the pin on the disk and using the height of the disk set relative to the drill guide.

The orientation and position of the locating channel can thus be easily verified.

Advantageously, target values for the coordinates of the upper tip of the pin on the disk and for the height of the disk can be calculated using design software for the drill guide, wherein the target values are then compared with the actual values read off.

Calculating the target values is thus computer-aided, taking the proposed drilled guide holes automatically into consideration. The actual values read off can thus be easily compared with the calculated target values. The actual values read off can be entered on an input screen of the design software, wherein the actual deviation of the pitch and the position of the locating channel is then calculated.

Advantageously, the disk can alternately be fabricated from a partially transparent material. The pin can have a laser oriented along an axis of the pin that projects a point of light onto the disk, wherein the laser on the inserted pin indicates a location on the disk, which is read off by means of the markings on the disk.

The location indicated by the pin can thus be easily determined by means of the laser. The disk can thus be arranged at any clearance from the drill guide.

Advantageously, the orientation and the position of the locating channel can be verified using the coordinates read off for the location on the disk, as indicated by the laser, and using the height of the disk set relative to the drill guide.

A precise verification of the locating channel is thus guaranteed.

Advantageously, the markings on the disk can display coordinate crosshairs with an x axis and a y axis, wherein a user reads off an x coordinate and a y coordinate for the location of the upper tip.

Concrete coordinates for the location can thus be read off. Alternately, the markings can also be scanned visually by means of an optical sensor.

Advantageously, with a support face of the drill guide, the drill guide can be placed on a suitably molded support on the device.

The drill guide can thus be precisely positioned in a particular location relative to the device.

Advantageously, the drill guide can have a magnifier, using which a user can read off the markings on the disk.

The markings on the disk can thus be displayed, magnified for better legibility.

BRIEF DESCRIPTION OF THE DRAWINGS

The invention is illustrated with the aid of the following drawings. The drawings depict.

DETAILED DESCRIPTION

Figure 1:
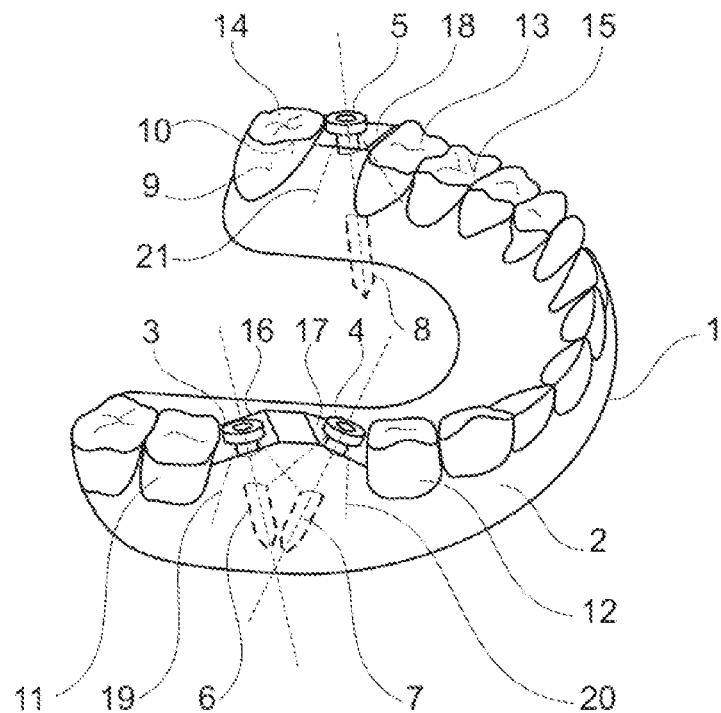
FIG. 1 a sketch of a drill guide with multiple sleeves.

FIG. 1 depicts a sketch of a drill guide 1 comprising a base part 2 and a first sleeve 3, a second sleeve 4 and a third sleeve 5 for creating a first drilled implant hole 6 a second drilled implant hole 7 and a third drilled implant hole 8. A first surface 9 of the base part 2 has a cast 10 of a preparation site. In the embodiment depicted, the drill guide incorporates the cast 10 of a patient's entire lower jaw. The drill guide 1 may also be fabricated, however, for only one part of the jaw or may only comprise the points of support on the adjacent teeth 11, 12, 13 and 14. A second surface 15 of the base part 2 has a first support surface 16, a second support surface 17 and a third support surface 18. The base part 2 also has a first access opening 19, a second access opening 20 and a third access opening 21, flared from the second surface 15 toward the first surface 9. The sleeves 3, 4 and 5 are inserted into the access openings 19, 20 and 21 with a cylinder-shaped sleeve part and are supported by a disk-shaped sleeve part on the support surfaces 16, 17 and 18, so that the position and the orientation of the sleeves 3, 4 and 5 are determined by the tilting and the position of the support surfaces 16, 17 and 18, and by the position of the access openings 19, 20 and 21. The sleeves 3, 4 and 5 are firmly bonded to the support surfaces 16, 17 and 18. The flared access openings 19, 20 and 21 are tapered.

Figure 2:
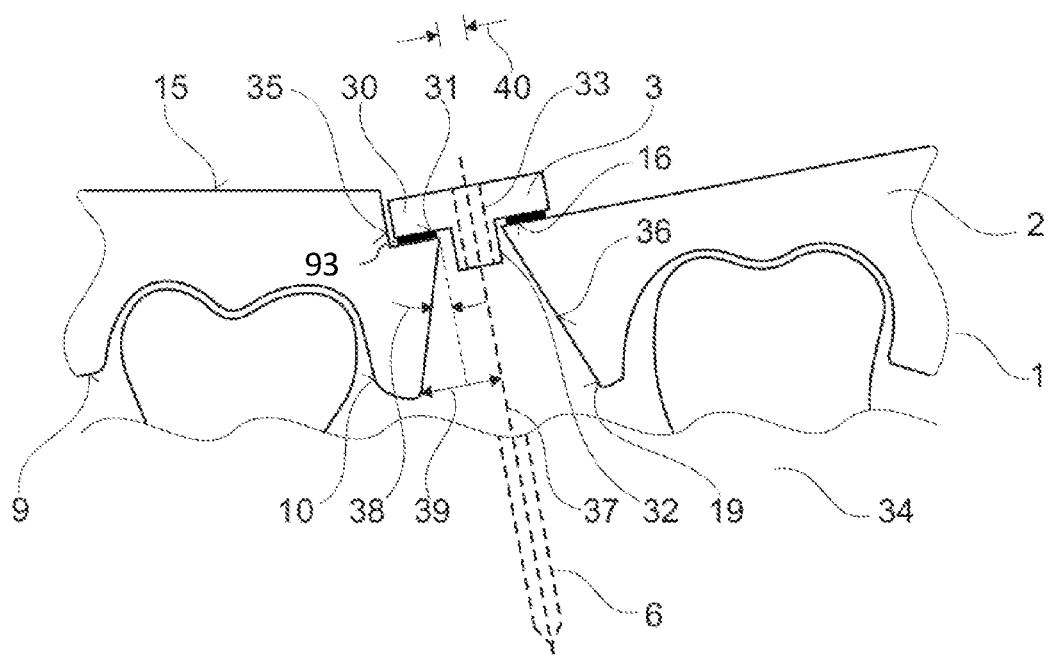
FIG. 2 a sketch of a section of the drill guide.

FIG. 2 depicts a sketch of a section of the drill guide 1 in FIG. 1, incorporating the base part 2 and the sleeve 3. The first surface 9 of the base part 2 depicts the cast 10, wherein the second surface 15 of the base part 2 located opposite depicts the first support surface 16. The sleeve 3 has a first disk-shaped part 30 that rests on a support face 31 on the support surface 16, and a second cylinder-shaped sleeve part 32 inserted into the first flared access opening 19. The sleeve 3 has a locating channel 33 designed to guide a drill in order to create the drilled implant hole 6 in a patient's jaw 34. The base part 2 has an end stop 35 in the form of a gradation with a right angle, to which the first disk-shaped sleeve part 30 is attached laterally. The end stop 35 can be designed as an analog to the disk-shaped sleeve part 30. The end stop can also be designed as a flat plane with one or more end stops on the sleeve. The flared access opening 19 has a lateral surface 36 that has an opening angle 38 to an axis 37 of the sleeve 3, and hence of the drilled implant hole 6, of 20° in the present case. The first access opening 19 is tapered and has a first radius 39 on the first surface 9 and a second radius 40 on the second surface 15 of the base part 2. Using a CAM machine tool, the access opening 19 is milled so that the second radius 40 corresponds as closely as possible to the radius of the second cylinder-shaped sleeve part 32. The position and orientation of the sleeve when inserted is thus fixed by the access opening 19, the end stop 35 and by the support surface 16.

Figure 3:
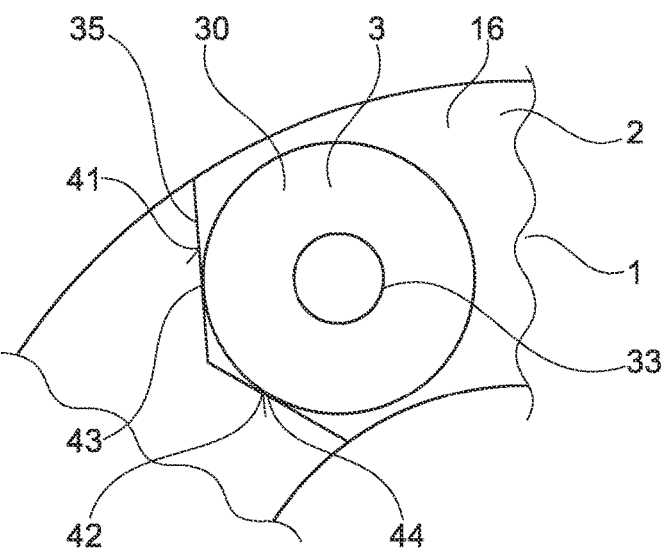
FIG. 3 a sketch of a plan view of the section of the drill guide in FIG. 1 and FIG. 2.

FIG. 3 depicts a sketch of a plan view of a section of the drill guide 1 in FIG. 1 and FIG. 2. The disk-shaped first sleeve part 30 of the sleeve 3 displays the cylinder-shaped locating channel 33. The disk-shaped sleeve part 30 rests on the support surface 16, which is designed as a sloping plane. Two flat planes 41 and 42 with a first end position 43 and a second end position 44 serve as an end stop 35.

Figure 4:
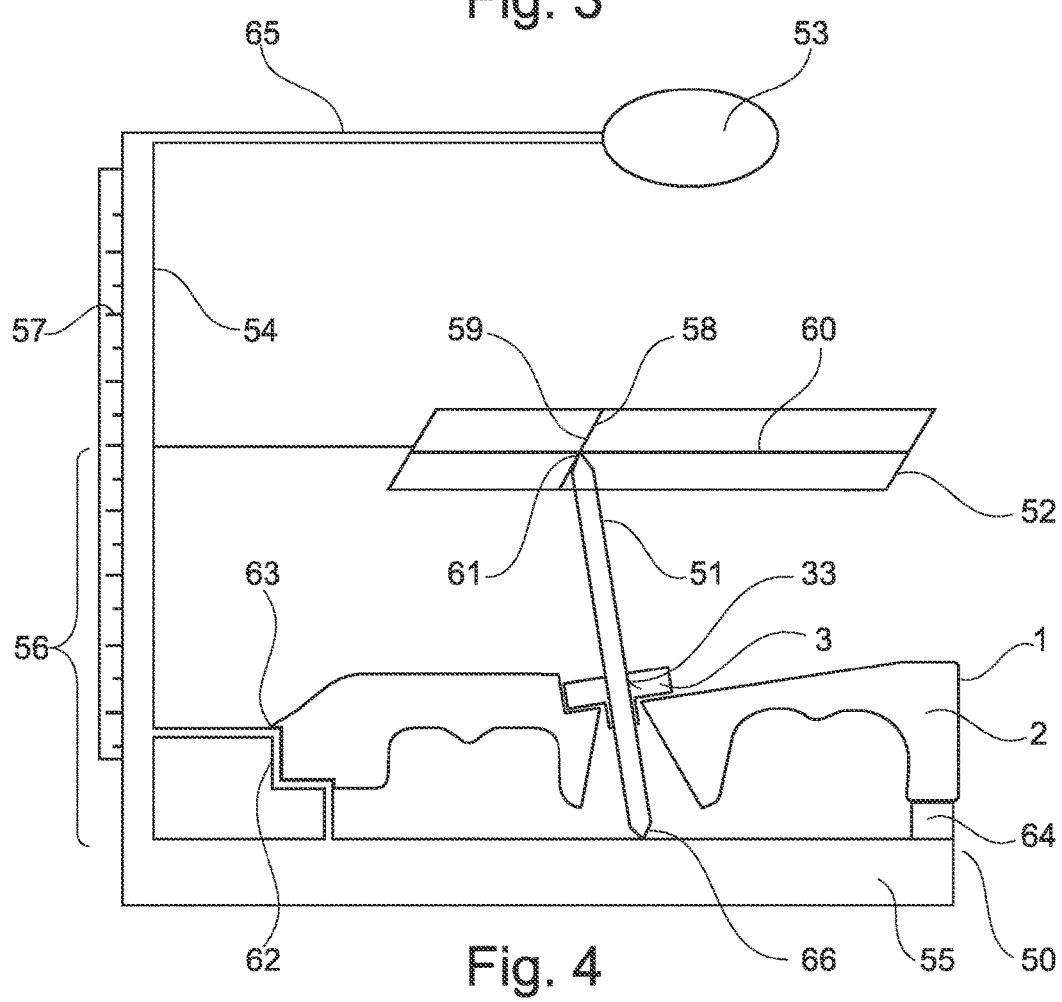
FIG. 4 a sketch of a device for checking the drill guide in FIG. 1 and FIG. 2.

FIG. 4 depicts a sketch of a device 50 for checking the drill guide 1 in FIG. 1 and FIG. 2, comprising the base part 2 and the sleeve 3 with the locating channel 33. The device 50 has a pin 51, a glass disk 52 and a magnifier 53. The glass disk 52 is mounted on a holder 54 connected to a baseplate 55.

The clearance 56 between the glass disk 52 and the baseplate 55 can be adjusted and can be read off using the measuring scale 57. The glass disk 52 has crosshairs 58 with an x axis 59 and a y axis 60, so that the precise location of an upper tip 61 of the pin 51 on the glass disk 52 can be read off. The device has a support 62, which is designed in the form of a gradation between the baseplate 55 and the holder 54. A support face 63, corresponding to the shape of the support 62, is provided on the drill guide. At the other end, the drill guide 1 rests on a second support 64. The magnifier 53 is attached to the holder 54 via an adjusting mechanism 65 so that the location of the magnifier can be adjusted for an enlarged view of the location of the upper tip 61 of the pin 51. The method for verifying the drill guide 1 proceeds in a number of process steps. In the first method the pin 51 is inserted into the sleeve 3, wherein a lower tip 66 of the pin 51 is in contact with the baseplate 55. In the second step, the clearance 56 of the glass disk 52 is adjusted so that the upper tip 61 comes into contact with the glass disk 52. In the third step, the coordinates for the location of the upper tip 61 are read off using the x axis 59 and the y axis 60. In the fourth step, the pitch and the position of the locating channel 33 of the sleeve 3 are calculated with the aid of the coordinates read off and the clearance 56. The actual values measured can then be compared with target values that have been calculated using design software.

Figure 5:
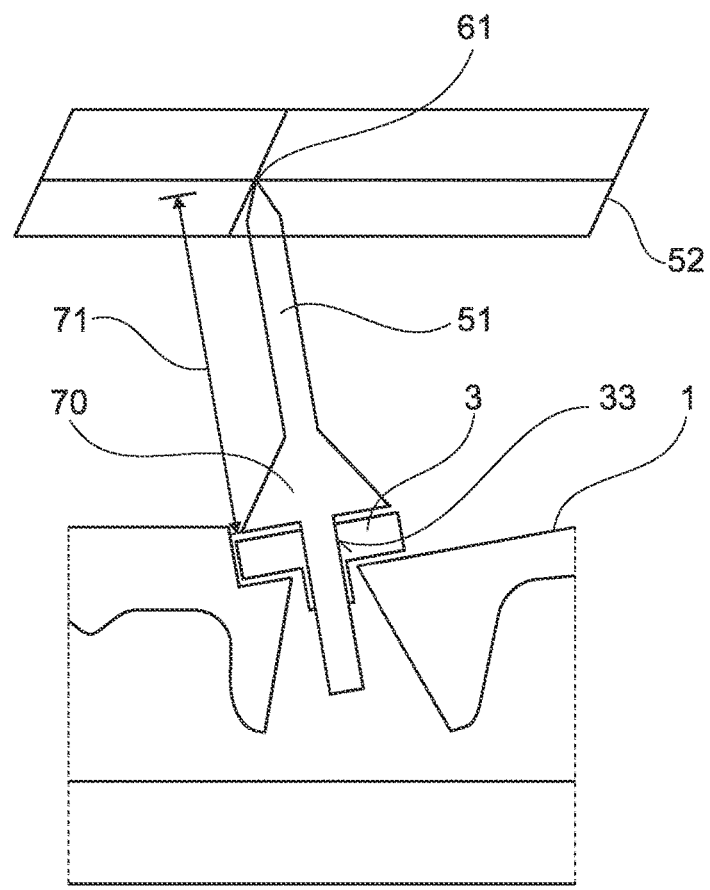
FIG. 5 a sketch of an alternate embodiment of the validation device.

FIG. 5 depicts a sketch of an alternate embodiment of the validation device. The difference from the device according to FIG. 4 is that the pin 51 has a tapered supporting part 70 in its central section that rests on the drill guide 3 when inserted. The length 71 of the upper part between the upper tip 61 and the supporting part 70 is known and, together with the coordinates of the location of the upper tip on the glass disk 51, is used to calculate the pitch and the position of the locating channel 33.

Figure 6:
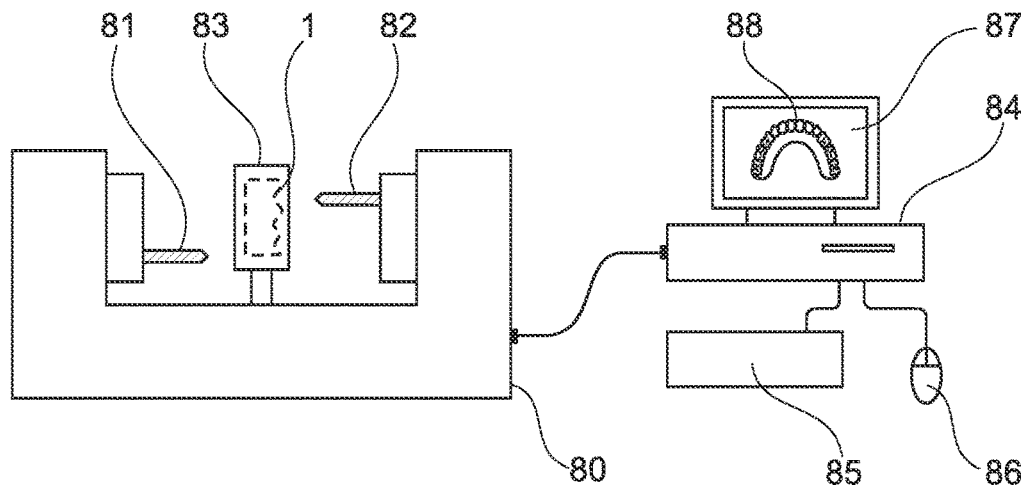
FIG. 6 a sketch of a CAM machine tool with three machining axes.

FIG. 6 depicts a sketch of a CAM machine tool 80 with three machining axes, incorporating a first milling tool 81 and a second milling tool 82, which, controlled by a computer 84, mill the abovementioned drill guide 1 in FIG. 1 to FIG. 5, shown as a dashed outline, from a blank 83. The computer 84 has input devices, such as a keyboard 85 and a mouse 86, such as those used to operate CAD software for inventory planning. The computer 84 is connected to a monitor 87, which displays a virtual model 88 of the proposed drill guide 1. The machine tool 80 can also have four machining axes. According to the present method according to the invention, the machine tool 80 with limited degrees of freedom can also be used to fabricate any drill guide with locating channels that are out of square. According to the conventional method, a machine tool with at least five machining axes must frequently be used for this purpose.

Figure 7:
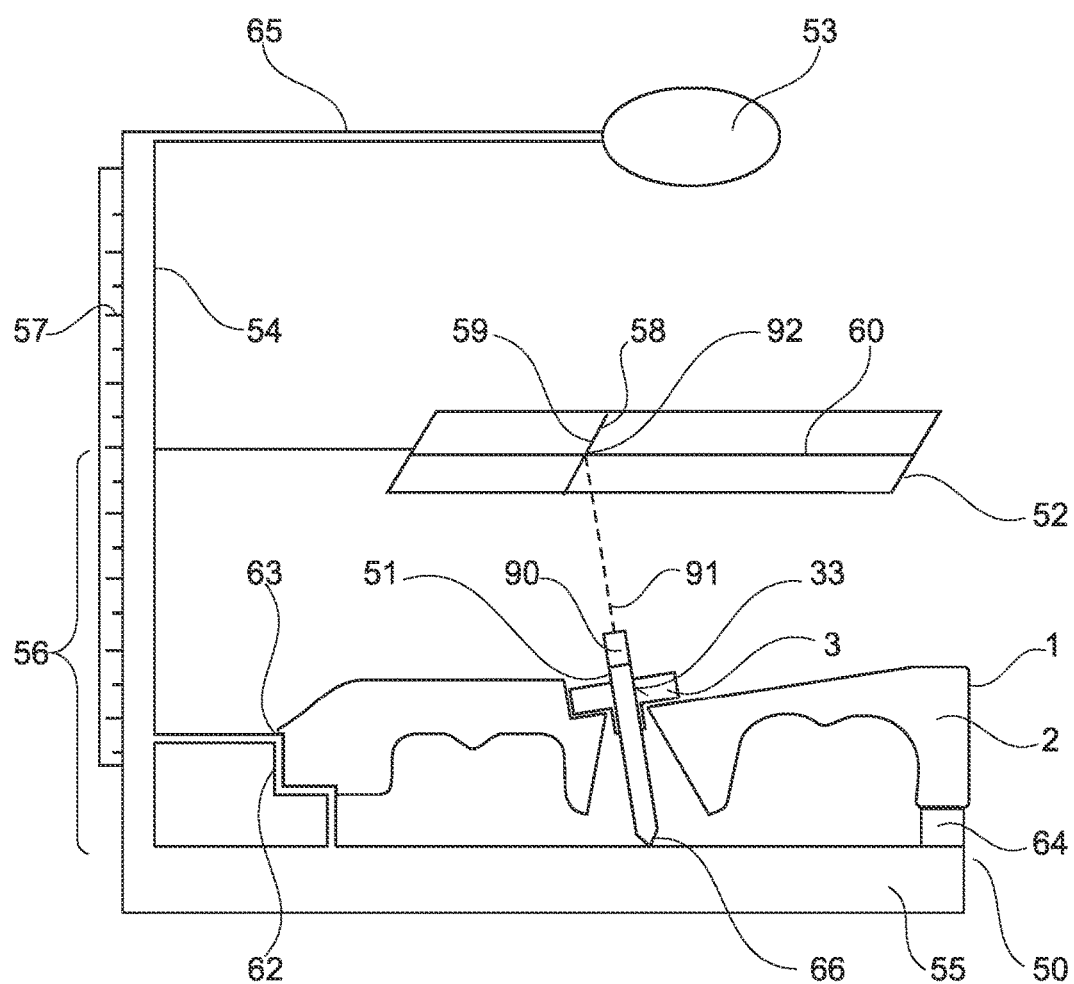
FIG. 7 a sketch of an alternate device for checking the drill guide using a laser.

FIG. 7 depicts a sketch of an alternate device to the device 50 in FIG. 4 for validating the drill guide 1 in FIG. 1 and FIG. 2. The difference from the device 50 in FIG. 4 is that the disk 52 is made from a partially transparent material and that the pin 51 has a laser 90 oriented along an axis of the pin that emits a laser beam 91, projecting a point of light 92 onto the disk 52, wherein the laser of the inserted pin 51 indicates a location 91 on the disk 52 that is read off by means of the coordinate axes 59, 60 on the disk 52. The orientation and the position of the locating channel 33 are determined and verified using the coordinates indicated by the laser 90 for the location 92 read off from the disk 52 and using the clearance 56 of the disk 52 relative to the drill guide 1.

The invention claimed is:

1. A drill guide for creating a drilled implant hole for a dental implant, the drill guide comprising:
    a base part that includes:
        a first surface that includes a cast of a preparation site, the preparation site includes a desired location of a drilled implant hole,
        a second surface that includes a support surface, the second surface being on an opposite side of the base part from the first surface, and
        an access opening extending from the second surface to the first surface, wherein a radius of the access opening increases in a direction towards the first surface beginning at the second surface such that a first radius of the access opening at the first surface is larger than a second radius of the access opening at the second surface; and
    a sleeve constructed to guide a drill, the sleeve includes:
        a disk-shaped first sleeve part,
        a cylinder-shaped second sleeve part, and
        a locating channel,
    wherein the sleeve is partially inserted into the access opening and the disk-shaped first sleeve part is fastened to the support surface of the base part, and
    wherein the second radius of the access opening is larger than a radius of the cylinder-shaped second sleeve part.

2. The drill guide in accordance with claim 1, wherein the base part includes an end stop in the form of a gradation of the second surface,
    wherein the end stop laterally contacts the disk-shaped first sleeve part, and
    wherein the end stop is located outside of the access opening.

3. The drill guide in accordance with claim 1, wherein a lateral surface of the access opening forms an opening angle of at least 15° with respect to an axis of the sleeve.

4. The drill guide in accordance with claim 1, wherein the sleeve has a third sleeve part with a locating channel, which is aligned in a direction away from the base part, starting from the support surface.

5. The drill guide in accordance with claim 1, wherein the sleeve is prefabricated and the base part can be fabricated using a machine tool with three or four machining axes.

6. The drill guide in accordance with claim 2, wherein the end stop is at a right angle to the support surface.

7. The drill guide in accordance with claim 2, wherein the end stop includes two flat planes which laterally contact different parts of the disk-shaped first sleeve part.

8. The drill guide in accordance with claim 1, wherein a diameter of the disk-shaped part is greater than a diameter of the access opening at the second surface.

9. The drill guide in accordance with claim 1, wherein the support surface is a flat plane perpendicular to a longitudinal axis of the access opening.

10. The drill guide in accordance with claim 1, wherein the cast of the preparation site includes a negative form of an occlusal surface of a first tooth adjacent to the desired location of the drilled implant hole.

11. The drill guide in accordance with claim 1, wherein the locating channel is constructed to guide a drill to create the drilled implant hole.

12. The drill guide in accordance with claim 7, wherein the two flat planes are perpendicular to the support surface.

13. The drill guide in accordance with claim 7, wherein the two flat planes are not parallel to the support surface.

14. The drill guide in accordance with claim 10, wherein the cast of the preparation site includes another negative form of an occlusal surface of a second tooth located adjacent to the desired location of the drilled implant hole and on an opposite side of the desired location of the drilled implant hole from the first tooth.

15. The drill guide in accordance with claim 1, wherein the base part is made of plastic and the sleeve is made of metal.

* * * * *